US011241176B2

(12) United States Patent
Barrett

(10) Patent No.: US 11,241,176 B2
(45) Date of Patent: Feb. 8, 2022

(54) DIRECT LIGHT DIFFERENTIAL MEASUREMENT SYSTEM WITH INCREASED NOISE IMMUNITY

(71) Applicant: Fresenius Medical Care Holdings, Inc., Waltham, MA (US)

(72) Inventor: Louis LeeGrande Barrett, West Point, UT (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 344 days.

(21) Appl. No.: 16/541,576

(22) Filed: Aug. 15, 2019

(65) Prior Publication Data

US 2019/0365293 A1    Dec. 5, 2019

Related U.S. Application Data

(63) Continuation of application No. 15/191,708, filed on Jun. 24, 2016, now Pat. No. 10,426,387.

(Continued)

(51) Int. Cl.
*A61B 5/1455* (2006.01)
*G01N 33/49* (2006.01)
(Continued)

(52) U.S. Cl.
CPC ........ *A61B 5/1455* (2013.01); *A61B 5/14557* (2013.01); *G01J 1/0214* (2013.01);
(Continued)

(58) Field of Classification Search
CPC . A61B 5/0059; A61B 5/1455; A61B 5/14551; A61B 5/14552; A61B 5/14532;
(Continued)

(56) References Cited

U.S. PATENT DOCUMENTS 4,553,033 A   11/1985   Hubble, III et al.
5,372,136 A   12/1994   Steuer et al.
(Continued)

FOREIGN PATENT DOCUMENTS

CN   101209201 A   7/2008
CN   101542245 A   9/2009
(Continued)

OTHER PUBLICATIONS

Chinese Patent Application No. 201680037268X, Office Action (dated Jun. 3, 2020).

(Continued)

*Primary Examiner* — Chu Chuan Liu
(74) *Attorney, Agent, or Firm* — Leydig, Voit & Mayer, Ltd.

(57) ABSTRACT

A measurement system for measuring blood characteristics includes a controller, an emitter, a sensor, and a reference sensor. The emitter emits light at a plurality of wavelengths from a first side of a blood flow channel to a second side of the blood flow channel. The sensor is provided on the second side of the blood flow channel. The reference sensor is provided on the first side of the blood flow channel. The controller compensates measurements from the sensor based upon measurements from the reference sensor. The reference sensor may be disposed in a position to increase noise immunity of the measurement system. The measurement system may be connected to or part of a dialysis system.

22 Claims, 9 Drawing Sheets

Related U.S. Application Data

(60) Provisional application No. 62/185,373, filed on Jun. 26, 2015, provisional application No. 62/184,680, filed on Jun. 25, 2015.

(51) Int. Cl.

| | | |
|---|---|---|
| *G01N 21/27* | (2006.01) | |
| *G01J 1/02* | (2006.01) | |
| *G01J 3/02* | (2006.01) | |
| *G01J 3/28* | (2006.01) | |
| *G01J 3/42* | (2006.01) | |
| *G01N 15/06* | (2006.01) | |
| *G01N 21/31* | (2006.01) | |
| *G01N 21/3577* | (2014.01) | |
| *A61B 5/00* | (2006.01) | |
| *G01J 1/44* | (2006.01) | |
| *G01N 15/00* | (2006.01) | |

(52) U.S. Cl.
CPC ............ *G01J 3/0205* (2013.01); *G01J 3/28* (2013.01); *G01J 3/42* (2013.01); *G01N 15/06* (2013.01); *G01N 21/274* (2013.01); *G01N 21/314* (2013.01); *G01N 21/3577* (2013.01); *G01N 33/49* (2013.01); *A61B 5/0022* (2013.01); *A61B 2560/0223* (2013.01); *G01J 2001/444* (2013.01); *G01N 2015/0065* (2013.01); *G01N 2015/0693* (2013.01); *G01N 2201/062* (2013.01); *G01N 2201/0624* (2013.01)

(58) Field of Classification Search
CPC ............ A61B 5/14557; A61B 5/14535; A61B 5/0022; A61B 5/72; A61B 2560/0223; G01N 2201/062; G01N 2201/0624; G01N 2201/0693; G01N 21/274; G01N 21/314
See application file for complete search history.

(56) References Cited

U.S. PATENT DOCUMENTS

| | | |
|---|---|---|
| 5,519,644 A | 5/1996 | Benton |
| 5,638,816 A | 6/1997 | Kiani-Azarbayjany et al. |
| 5,686,656 A | 11/1997 | Amirav et al. |
| 5,879,294 A | 3/1999 | Anderson et al. |
| 6,016,697 A | 1/2000 | McCulloch et al. |
| 6,600,940 B1 * | 7/2003 | Fein ................ A61B 5/14552 600/323 |
| 6,862,534 B2 | 3/2005 | Sterling et al. |
| 7,341,559 B2 | 3/2008 | Schulz et al. |
| 7,577,469 B1 | 8/2009 | Aronowitz et al. |
| 8,143,567 B2 | 3/2012 | Williams et al. |
| 8,518,247 B2 | 8/2013 | Akita et al. |
| 8,743,354 B2 | 6/2014 | Barrett et al. |
| 9,212,988 B2 | 12/2015 | Akita et al. |
| 2003/0103874 A1 | 6/2003 | Rossi |
| 2014/0266983 A1 | 9/2014 | Christensen |
| 2014/0267003 A1 | 9/2014 | Wang et al. |
| 2015/0253860 A1 | 9/2015 | Merics et al. |
| 2016/0296687 A1 | 10/2016 | Scarpaci |

FOREIGN PATENT DOCUMENTS

| | | |
|---|---|---|
| CN | 102301233 A | 12/2011 |
| CN | 102612677 A | 7/2012 |
| CN | 102822691 A | 12/2012 |
| CN | 103105612 A | 5/2013 |
| CN | 103857464 A | 6/2014 |
| CN | 104280122 A | 1/2015 |
| DE | 10-2010-026723 A1 | 1/2012 |
| JP | H06-342938 A | 12/1994 |
| JP | H10-65218 A | 3/1998 |
| JP | 11-122424 A | 4/1999 |
| JP | 2000-346798 A | 12/2000 |
| JP | 2002-214126 A | 7/2002 |
| JP | 2005-517923 A | 6/2005 |
| JP | 2008-108861 A | 5/2008 |
| JP | 2013-543578 A | 12/2013 |
| JP | 2014-513584 A | 6/2014 |
| WO | WO 2008/039195 A1 | 4/2008 |
| WO | WO 2012/116336 A2 | 8/2012 |
| WO | WO 2014/157282 A1 | 10/2014 |

OTHER PUBLICATIONS

Chinese Patent Application No. 201680037268X, Office Action (dated Mar. 1, 2021).
Japanese Patent Appliation No. 2017-566349, Office Action (dated Jan. 7, 2020).
U.S. Appl. No. 15/191,708, filed Jun. 24, 2016, Pending.

* cited by examiner

DIRECT LIGHT DIFFERENTIAL MEASUREMENT SYSTEM WITH INCREASED NOISE IMMUNITY

CROSS-REFERENCE TO RELATED APPLICATIONS

This application is a continuation of U.S. application Ser. No. 15/191,708, filed Jun. 24, 2016, which claims the benefit of and priority to U.S. Provisional Patent Application Nos. 62/184,680 filed Jun. 25, 2015 and 62/185,373 filed Jun. 26, 2015. All of the foregoing applications are incorporated by reference in their entireties.

TECHNICAL FIELD

The disclosure generally relates to optical blood monitoring systems used to monitor extracorporeal patient blood flow and take real-time measurement of hematocrit, oxygen saturation levels and/or other blood constituents. The disclosure more particularly is directed to improving the reliability and accuracy of such systems.

BACKGROUND

Patients with kidney failure or partial kidney failure typically undergo hemodialysis treatment in order to remove toxins and excess fluids from their blood. To do this, blood is taken from a patient through an intake needle or catheter which draws blood from an artery or vein located in a specifically accepted access location—e.g., a shunt surgically placed in an arm, thigh, subclavian and the like. The needle or catheter is connected to extracorporeal tubing that is fed to a peristaltic pump and then to a dialyzer that cleans the blood and removes excess fluid. The cleaned blood is then returned to the patient through additional extracorporeal tubing and another needle or catheter. Sometimes, a heparin drip is located in the hemodialysis loop to prevent the blood from coagulating.

As the drawn blood passes through the dialyzer, it travels in straw-like tubes within the dialyzer that serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste. The red cells remain in the straw-like tubes and their volume count is unaffected by the process.

A blood monitoring system is often used during hemodialysis treatment or other treatments involving extracorporeal blood flow. One example is the CRIT-LINE® monitoring system produced by Fresenius Medical Care of Waltham, Mass. The CRIT-LINE® blood monitoring system uses optical techniques to non-invasively measure in real-time the hematocrit and the oxygen saturation level of blood flowing through the hemodialysis system. The blood monitoring system measures the blood at a sterile blood chamber attached in-line to the extracorporeal tubing, typically on the arterial side of the dialyzer.

In general, blood chambers along with the tube set and dialyzer are replaced for each patient. The blood chamber is intended for a single use. The blood chamber defines an internal blood flow cavity comprising a substantially flat viewing region and two opposing viewing lenses. LED emitters and photodetectors for the optical blood monitor are clipped into place onto the blood chamber over the lenses. Multiple wavelengths of light may be directed through the blood chamber and the patient's blood flowing through the chamber with a photodetector detecting the resulting intensity of each wavelength.

Suitable wavelengths to measure hematocrit are about 810 nm, which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System and Method for Non-Invasive Hematocrit Monitoring," which issued on Dec. 13, 1999, and is incorporated herein by reference, uses this light intensity information to calculate the patient's hematocrit value in real-time. The hematocrit value, as is widely used in the art, is a percentage determined by the ratio between (1) the volume of the red blood cells in a given whole blood sample and (2) the overall volume of the blood sample.

In a clinical setting, the actual percentage change in blood volume occurring during hemodialysis can be determined, in real-time, from the change in the measured hematocrit. Thus, an optical blood monitor is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real time, Light Emitting Diodes (LEDs) and photodetectors for them are mounted on two opposing heads of a sensor clip assembly that fit over the blood chamber. For accuracy of the system, the LEDs and the photodetectors are located in a predetermined position and orientation each time the sensor clip assembly is clipped into place over the blood chamber. The predetermined position and orientation ensures that light traveling from the LEDs to the photodetectors travels through a lens of the blood chamber.

In existing systems, the optical monitor is calibrated for the specific dimensions of the blood chamber and the specific position and orientation of the sensor clip assembly with respect to the blood chamber. For this purpose, the heads of the sensor clips are designed to mate to the blood chamber so that the LEDs and the photodetectors are at known positions and orientations with respect to one another.

While there are numerous light emitters which can be used, LEDs are often preferred due to their cost factors with their wide use in industry. In most non-medical applications, precise amplitude of the generated light is not important. For example, indicator lights showing that a device is on is only required to glow so that it is visible to the end user. Whether the amplitude (brightness) of the light changes slightly over time or temperature is of no consequence in this use. Another example where precision of amplitude is less critical is in driving fiber optic cables to propagate phone calls, video and the like over extended distance. In this application, the light source is commonly keyed on and off in patterns or time widths creating modulations where detection is by light amplitude thresholds. If the light amplitude is high enough to exceed the threshold, one digital state is registered. If not, then the opposite digital state is registered. A slight change in amplitude where the threshold is still crossed is of no consequence to the operation of the system.

However, the use of LEDs (or any light source) in blood monitoring systems such as described herein requires knowing the precise amplitude. All small variations in the amplitude are accounted for. Otherwise, errors can result in the measurements of blood parameters. For blood parameters to be repeatedly measured with acceptable accuracy, effects on the amplitude of the light that are acceptable in some applications such as telecommunications must be dealt with in blood monitoring systems.

Changes in the amplitude of the light from LEDs can be attributed to three of their physical properties.

The first property gives an effect of a "short term" amplitude shift, which affects the amplitude. During the manufacturing process of LEDs, specially formulated Silicon or Indium Gallium Arsenide compounds are melted together to form electrical junctions, making the device an LED. Impurities in the environment during the manufacturing process, although the process is performed in a clean room, can contaminate the junction. The effect is to change the amplitude that would otherwise be obtained if the junction is pure when energized with the proper current. Over time, with heat applied during normal operation of the junction, the impurities are "burned off," causing the LED to change its output amplitude as the impurities diminish.

The second property causes a "long term" amplitude shift. This shift results from the quantum mechanics of the materials in the LEDs as they change with age. There is nothing to be done about this effect. The shift is small and requires several years for it to have an effect on the amplitude that would be noticeable in the context of applications such as blood monitoring systems.

The third property causing changes to the amplitude of the light is temperature sensitivity. The temperature at the internal LED junction directly affects the speed of the electro-chemical reaction at the junction, which in turn affects the number of electrons changing orbit. The energy released by this action is selected by the compounds used to make the LED to yield a specific wavelength of light. For example, at higher temperatures there is more electron activity in the device junction, resulting in more electron movement and, thus, greater amplitude of the light.

To address the "short term" effect on amplitude, conventional blood monitoring systems often rely on a base calibration model to yield a known, quantified amplitude for an LED. A "burn-in" process deliberately raises the LED junction temperatures using high current (but not high enough to harm the device's junction) to rapidly dissipate any manufacturing impurities in the junction and bring "short term" stability to the LED.

To address the "long term" effect on amplitude, the variation is slow enough that conventional blood monitoring systems are usually returned for service or for other reasons prior to this effect become noticeable in the context of the system's performance.

The temperature effect on the amplitude of the light from LEDS is addressed in many conventional blood monitoring systems by employing a compensation model that relies on a relationship between temperature and amplitude variations established through measurements. The blood monitoring system uses a thermistor sensor mounted in close proximity to the LEDs to measure the average temperature of the LEDs. The temperature signal from the thermistor is provided to the compensation model that compensates for variations in the amplitude of the light from the LEDs as a function of their temperatures. The compensation model includes empirical data collected for each LED. The compensation model of each blood monitor system is calibrated for the temperature profile of its LEDs. Thus, each monitor channel has a temperature calibration model based on the temperature profile for the LED for which it provides compensation. Moreover, the average temperature of all LEDs in a system is typically used for the compensation, causing errors in measurement in the event of a single LED fluctuation. Also, measuring light output by sensing the temperature profiles of the LEDs and then mapping the actual temperatures to light amplitude can become inaccurate as the LEDs age (the "long term" effect).

SUMMARY

According to one aspect of the blood monitoring system described herein, the system compensates for the variation in the light amplitude level from the LEDs in the optical monitor without requiring calibration of each monitor to account for individual LED characteristics.

A first advantage of an embodiment is that the system is self-normalizing. Regardless of temperature changes, an embodiment provides a ratio of a received light measurement to an initial reference light measurement. Such an embodiment obviates the need for creating a calibration model to account for temperature variations.

A second advantage of an embodiment is that the system does not become uncalibrated in the event an LED changes output amplitude due either to age or as the result of impurities in the manufacturing process, or transients in the LED operating current. That is, an LED whose light amplitude may have changed over time for any reason can still be used for accurate measurement.

A third advantage of an embodiment is that it avoids the need to "burn-in" LEDs. Embodiments of the present invention allow for accurate system operation without such burn-in because a real time reference light measurement normalizes any short term changes in LED amplitude output.

A fourth advantage of an embodiment is that it permits the use of LEDs with minor spectral variations in wavelength energies and bandwidths.

In one illustrated embodiment, the light level from the LEDs is measured directly and provided for comparison with light levels measured through a blood flow channel Measurements are based on the ratio of the light amplitude before and after the light is passed through the blood flow channel, thus normalizing the measurement to account for variations in the light from the LEDs. In this regard, one feature of the illustrated embodiment is that the direct measurement of the LED output amplitudes keeps the monitor in proper calibration for a longer time and extends the life cycle of the monitor.

Directly measuring the LED light output eliminates a significant calibration problem caused by a time dynamic characteristic of monitors using thermistors to map temperature into light output amplitude compensation. Also, direct measurement of the LED light allows for the use of less precise LEDs in contrast to temperature-tested and stable LEDs whose costs may make them impractical for commercial use in blood monitoring systems. The ability to rely on less precise LEDs leads to the expeditious addition of wavelengths for measuring absorption characteristics of other blood constituents.

The blood monitoring system described herein measures blood characteristics and includes a controller, an emitter (e.g., an LED), a sensor, a reference photo sensor and a mask for optically isolating the reference photo sensor from light other than light directly sourcing from the emitter. The emitter emits light at a plurality of wavelengths that enters a blood flow channel from a first side of the channel and exits the channel on a second side. The sensor is provided on the second side of the blood flow channel and detects characteristics of the light that are affected by the blood constituents in the channel. The reference photo sensor is provided on the first side of the blood flow channel and receives light from the emitter before is passes through the channel. The mask isolates the reference photo sensor from light sources other than the emitter (e.g., other light source or reflection). The controller uses information from the reference photo sensor to compensate for changes in the light from the emitter so that measurements from the sensor are thereby "normalized" to be measurements only of the effects on the light from the blood constituents.

In an embodiment, the system uses a Indium Gallium Arsenide photodiode as the reference photo sensor to directly measure light from the emitter (e.g., LED) and the direct measurement is used to normalize the measurement of the light at the sensor, thereby eliminating any need for an indirect normalization such as a temperature proxy measurement and associated calibration. By directly measuring LED light amplitude, the blood monitoring system does not need to wait for the LED temperatures to stabilize before using the system. If the monitor is used immediately after it is turned on, this direct measurement ensures the measured effect on the light from the blood constituents is free of any influence from changes at the LED. With the indirect approach to normalizing the measurements, the blood monitoring system has to stabilize to a condition expected by the electronics providing the indirect normalization, which usually takes a few minutes. In contrast, the direct measurement can reliably normalize the measurement immediately so that no warm up or stabilizing time period is necessary. Furthermore, in some clinical settings, blood monitoring systems are left on continually, which leads to faster aging of the LEDs. Here again, the direct measurement approach normalizes the measurement to account for this faster aging.

BRIEF DESCRIPTION OF THE SEVERAL VIEWS OF THE DRAWINGS

The present invention will be described in even greater detail below based on the exemplary figures and embodiments. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
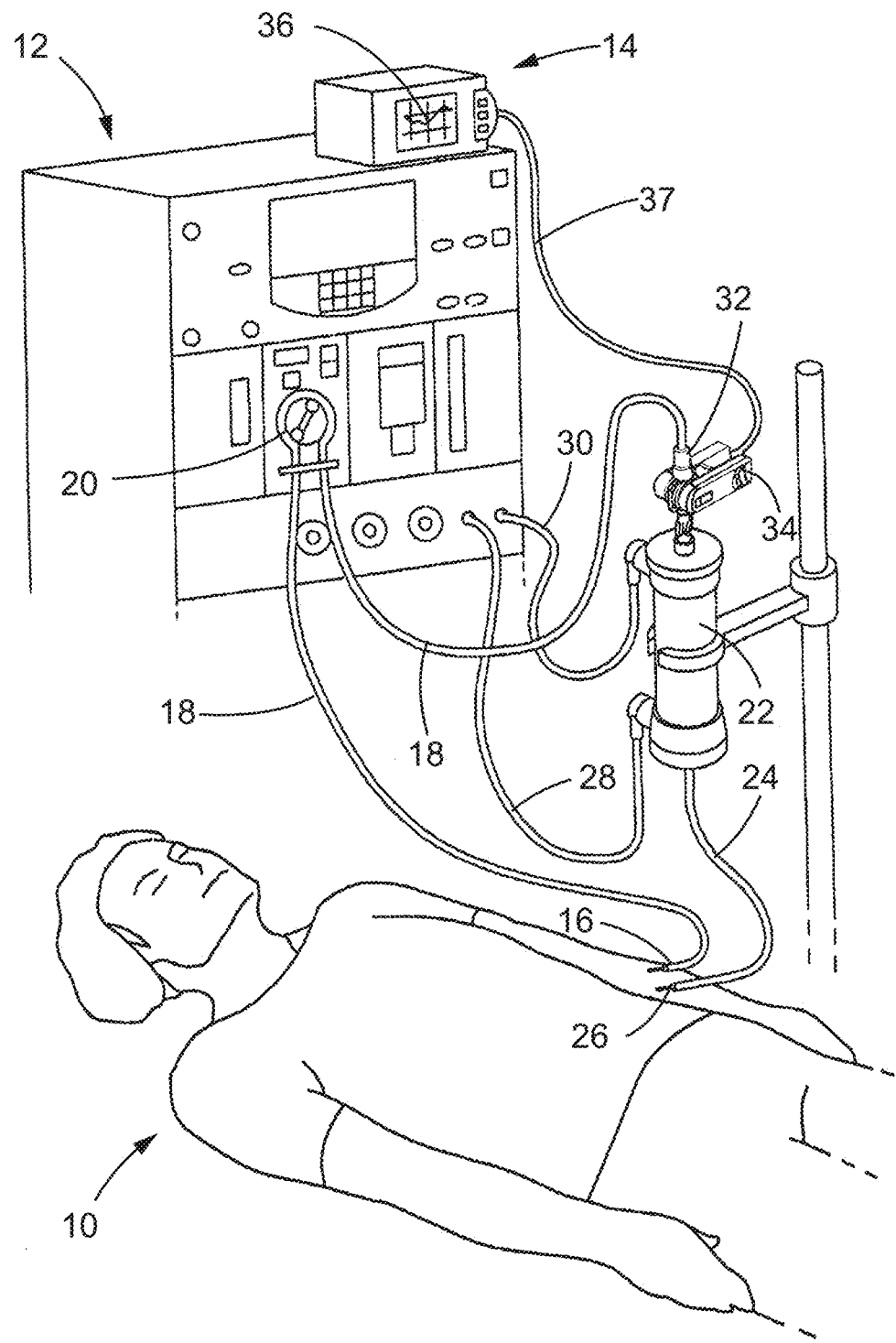
FIG. 1 illustrates an exemplary blood monitoring system as part of a dialysis treatment system.

FIG. 1 illustrates an exemplary environment usable with embodiments of a blood monitoring system incorporating the invention. It will be appreciated by those skilled in the art that the monitoring system has applications other than in a dialysis system, such as for example, measuring hematocrit and oxygen levels during perfusion with a heart-lung machine, or during extracorporeal membrane oxygenation (ECMO), or continuous renal replacement therapy (CRRT).

In a conventional manner, a patient 10 in FIG. 1 is attached to the dialysis treatment system 12 via a blood extraction needle 16 and blood injection needle 26. During a dialysis treatment with the dialysis treatment system 12, blood is extracted from the patient 10 via blood extraction needle 16, passed through the blood pump 20, the blood chamber 32 and dialyzer blood filter 22 using tubes 18, and then returned back to the patient 10 via tube 24 and blood injection needle 26. The dialyzer 22 filters the blood by fluid exchange with dialysis solution from fresh dialysis tube 28 and deposits filtered waste out to used dialysis tube 30.

A blood monitoring system 14 incorporating the invention is used with a dialysis treatment system 12 for monitoring certain blood characteristics relevant to the dialysis process. The blood monitoring system 14 includes a display 36, a cable 37 and a clip assembly 34 that mates to a blood chamber 32 in the blood flow path provided by the tubes 18. The clip assembly 34 includes light sources and detectors that are positioned on opposite sides of the blood chamber 32 when the clip assembly is mated to the blood chamber. Light passing through the blood chamber from the light sources in the clip assembly 34 is absorbed by the blood undergoing dialysis. Detectors in the clip assembly 34 detect the absorption and circuitry in either the clip assembly or the display 36 process absorption signals from the detectors to provide information at the display meaningful to the clinician responsible for the dialysis process.

Figure 2:
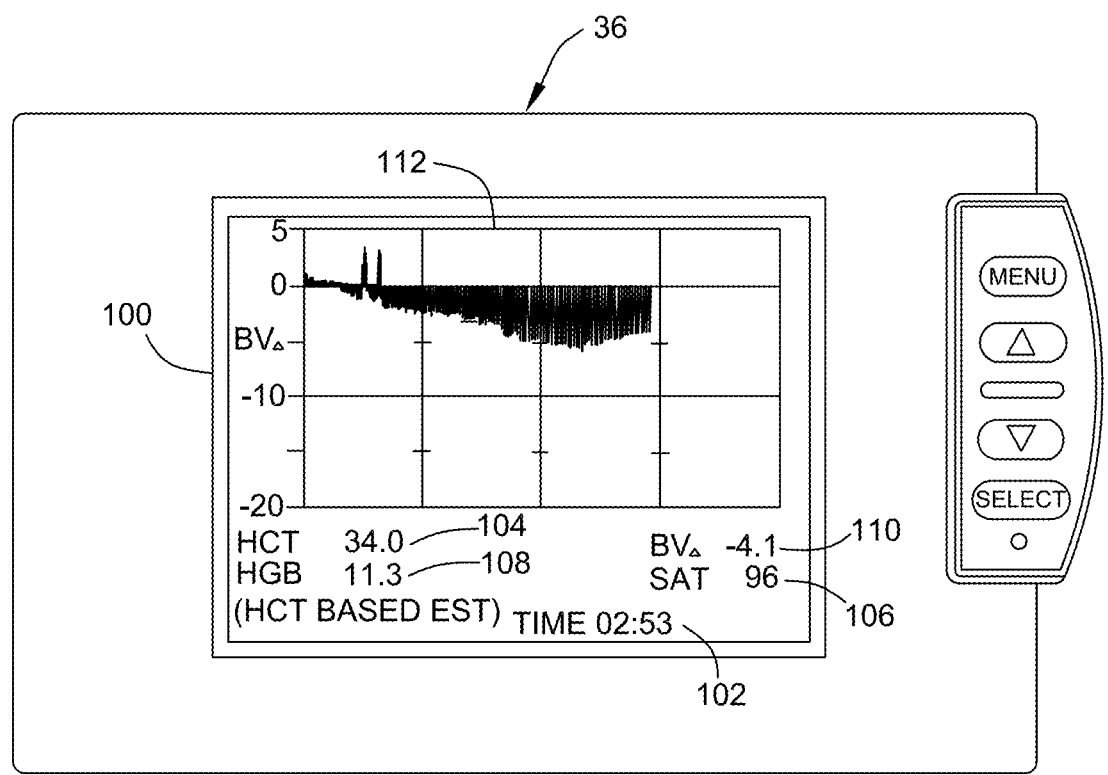
FIG. 2 illustrates an exemplary control interface of the blood monitoring system in FIG. 1.

FIG. 2 illustrates an embodiment of the display 36 of the blood monitoring system 14. The illustrated embodiment of the display 36 includes a screen 100 for displaying information such as, for example, a plot 112 of change of blood volume (BVA) versus time, current elapsed time 102 of a dialysis session (assuming the system is in place with a dialysis system), current hematocrit (HCT) measurement 104, current oxygen saturation (SAT) measurement 106, current estimated hemoglobin (HGB) level 108, current $BV_A$ measurement 110, and the like measurements useful to the clinician during the dialysis process. A user may operate the blood monitoring system 14 via the display 36, for example, to change the types of information displayed by the display, or the manner of the display (plots or alphanumeric text).

The illustrated display 36 includes various control buttons for control of the blood monitoring system 14. Alternatively or in addition, the screen 100 may be a touch screen and control of the blood monitoring system 14 can be accomplished using the touch screen 100 as a control interface. In other embodiments not illustrated, the blood monitoring system 14 is controlled or monitored using remote and/or other non-contact interface mechanisms. See, for example US 4/0267003 to Wang et al., entitled "Wireless Controller to Navigate and Activate Screens on a Medical Device," US 2014/0266983 A1 to Christensen, entitled "Wearable Interface for Remote Monitoring and Control of a Medical Device," and US 2015/0253860 A1 to Merics et al. entitled "E-field Sensing of Non-contact Gesture Input for Controlling a Medical Device," all of which are incorporated herein by reference in their entirety and for all they disclose.

Figure 3:
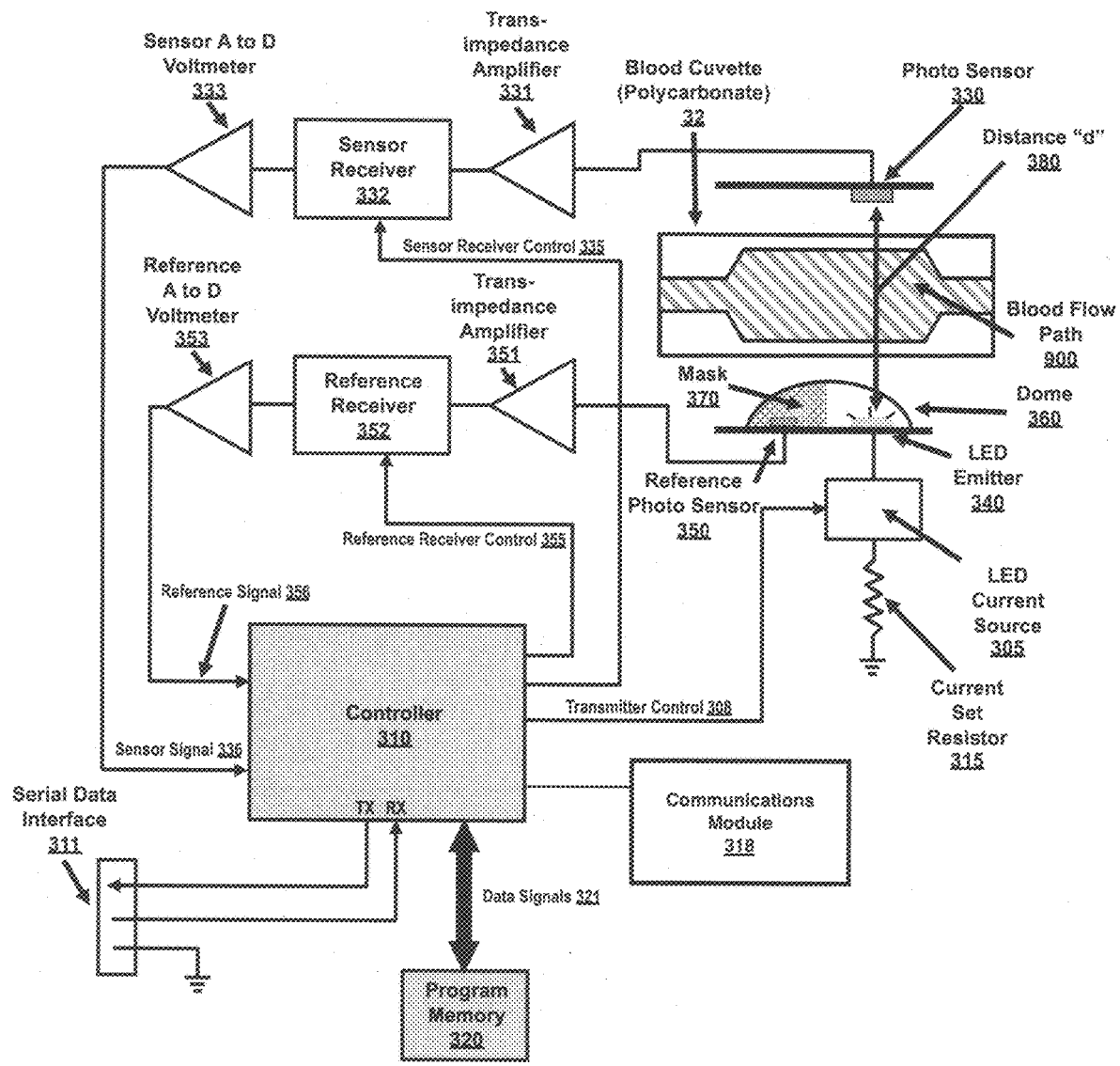
FIG. 3 is a schematic of an aspect of the blood monitoring system according to an embodiment in which the system self calibrates by relying on direct measurement of the light output from the system's light sources used for monitoring blood constituents.

FIG. 3 schematically illustrates the blood monitoring system 14. The system 14 includes a controller 310 that may be located either within the clip assembly 34 or the display 36. The system 14 also includes at the clip assembly 34 an LED emitter 340, a sensor 330 for sensing light from the LED after it passes through the blood chamber 32, a reference photo sensor 350 for directly sensing light from the LED and a mask 370 for shielding the photo sensor from light other than from the LED 340. The LED emitter 340 emits light at a plurality of wavelengths from a first side of the blood chamber 32 and through a blood flow path 900 provided by the chamber. The light exits the blood chamber 32 at a second side of the chamber after traveling a fixed distance 380 of "d" between the LED 340 and the sensor 330. The distance "d" can be arbitrary to the system design. But once the distance is selected, it remains constant. The LED 340 and sensor 330 are each supported on opposing arms of the clip assembly 34 at the area of the clip assembly that mates with the blood chamber 32. The reference photo sensor 350 is also supported by the clip assembly 34 and is specifically supported on the same side as the LED 340. The mask 370 is also supported by the clip assembly 34 and on the same side as the LED 340 and the reference photo sensor 350. The mask may be realized in several alternative embodiments, including those illustrated herein. In the various embodiments, the mask 370 shields the reference photo sensor 350 from receiving light other than directly from the LED emitter 340—e.g., no light externally reflected light or light from other sources.

The controller 310 synchronizes and controls the monitoring system 14 as a whole. Measurements of the light reaching the sensor 330 are processed by signal processing hardware and fed to the controller 310. Similarly, supporting signal processing hardware feeds compensation measurements from the reference photo sensor 350 to the controller 310. The controller 310 than normalizes the "raw" measurement from the sensor 330 using the measurement received from the photo sensor 350. The reference photo sensor 350 and the sensor 330 may each be a Silicon or a Indium Gallium Arsenide photodiode, or each may be an array of Silicon or Indium Gallium Arsenide photodiodes.

In the illustrated embodiments, the emitter 340 includes a light-emitting-diode (LED) or an array of LEDs. The emitter 340 may include other light sources, such as LASER emitters, fluorescent light sources, incandescent light sources and the like.

The blood flow chamber 32 can be made of polycarbonate. The purpose of the blood chamber is to provide a window into the blood flow during a process (e.g., dialysis) to be monitored and to maintain the spacing "d" 380 as a constant during the measurement process involved in the monitoring.

In one embodiment as illustrated in FIG. 3, a dome 360 is covering the LED emitter 340. One part of the dome 360 contains the mask 370 surrounding the reference photo sensor 350 in all directions other than in the direction of the LED 340. The dome 360 may be of various shapes, such as rectangular and semi-spherical. The dome 360 may also be of various materials, such as epoxy, plastic, glass or plexiglass, or other inorganic materials that are reproducible with respect to their optical properties. The transparent dome 360 provides some protection for the LED emitter 340, such as against dust contamination, thermal stress, electrical shorts, and mechanical damages from moving parts while providing a path for light from the LED to illuminate the first side of the blood chamber 32. The dome 360 provides the same protections for the reference photo detector 350 under the masked 370 portion of the dome.

In the embodiment illustrated in FIG. 3, the mask 370 covers a portion of the transparent dome 360. The mask 370 may be a portion of the transparent dome 360 that is coated with a dense, light stopping material, on the outer surface of the dome or on its inner surface if the dome is hollow. The mask 370 may be an opaque coating of the dome 360 that blocks reflected light, both visible and infrared, ensuring that the only light visible to the reference photo sensor 350 is light emitted from the LED emitter 340.

Alternatively, the mask 370 may stand alone without the transparent dome 360 or separated from the transparent dome 360. The precise mechanical structure of the mask can have these and other variations as long as the mask functions to isolate the reference photo sensor 350 from light originating from sources other than the LED emitter 340.

In the illustrated embodiment of FIG. 3, the light amplitude intensity for the LED emitter 340 is controlled by a LED current source 305 with the intensity set by the current set resistor 315. The controller 310 is able to further adjust the LED current source 305 to compensate the light intensity using transmitter control 308 based on the reference signal 356 that is developed from the signal provided by the reference photo sensor 350.

Light passes from the LED emitter 340 through the unmasked portion of the dome 360 in FIG. 3 and the blood chamber 32 body to the photo sensor 330. The blood flow path 900 across the blood chamber has the fixed distance "d" 380 to ensure proper calibration. Blood parameters absorb and scatter the light, which attenuates the amplitude of the light at different wavelengths arriving at the photo sensor 330. The amount of amplitude attenuation at predetermined wavelengths is used to determine blood properties such as hematocrit. The determination process is more completely described in U.S. Pat. Nos. 5,372,136 and 6,246,894, which are incorporated by reference herein in their entirety and for everything they describe.

In response to the light reaching it after passing through the blood in the blood chamber 32, the photo sensor 330 generates in a conventional manner a current signal proportional to the intensity of the light it receives and sends the current signal to signal processing circuitry to be processed for use by the controller 310. For example, in the illustrated embodiment in FIG. 3, a trans-impedance amplifier 331 receives the current signal and amplifies it as necessary and converts the signal to a voltage signal. The voltage signal is then applied to a sensor receiver 332 where it is filtered and conditioned for passing on to an analog-to-digital (A to D) voltmeter 333. This voltmeter 333 converts the measured voltage proportional to the light received at the photo sensor 330 to a final digital sensor signal 336 formatted to be an input to the controller 310.

Similarly, light from the LED emitter 340 that reaches the reference photo sensor 350 under the mask area 370 of the dome 360 causes the reference photo sensor to react by generating a current signal, which is processed by signal processing circuitry in a manner similar to the current signal from the photo sensor 330. All material in the optical path from the LED emitter 340 to the reference photo sensor 350 have unchanging optical properties such that the signal received at the reference photo sensor 350 varies solely with changes in the emission characteristics of the LED emitter. The mask 370 prevents reflections from outside the dome 360 and light sourcing from other than the LED emitter from summing into the direct signal between the reference photo sensor 350 and the LED emitter 340.

In the embodiment illustrated in FIG. 3, the light from the LED emitter 340 received at the reference photo sensor 350 is converted in a conventional manner to a proportional current signal by the reference photo sensor 350. This current signal is applied to a trans-impedance amplifier 351 where it is amplified as necessary and converted to a voltage output signal. The voltage signal is then applied to a reference receiver 352 where it is filtered and conditioned as a voltage measurement by an analog-to-digital (A to D) voltmeter 353. The voltmeter 353 converts the measured voltage proportional to the light received to a digital reference signal 356, which is read by the controller 310.

The controller 310 compensates for the measurements from the sensor 330 at the sensor signal 336 that source from changes in the intensity of the light at the LED emitter 340, using the measurements provided by the reference signal 356 from the reference photo sensor 350. The compensation accounts for variations in the light emitted from the LED emitter 340 and is continuous and substantially in real time.

The controller 310 in the embodiment illustrated in FIG. 3 also has the option to adjust the amplitude of the light at the LED emitter 340 by adjusting the LED current source 305 to provide more power to the LED emitter. A transmitter control 308 signal from the controller 310 to the LED current source 305 accomplishes this task.

The LED emitter 340 may experience short term or long term variations in the amplitude of its emitted light for various reasons. For example, there may be power fluctuations in the LED emitter 340, which causes the light intensity from the LED emitter to change according to the power fluctuations. Or light from the LED emitter 340 may gradually intensify or fade in intensity due to degradation of the LED emitter. The system in the illustrated embodiment of FIG. 3 continuously compensates for these variations during operation by providing the controller 310 with the ability to compensate for changes in measurements from the reference photo sensor 350, which thereby results in the system to maximize its accurate measurements of the attenuation of the light at the photo sensor 330 caused only by the properties of the blood in the blood flow path 900.

Figure 4:
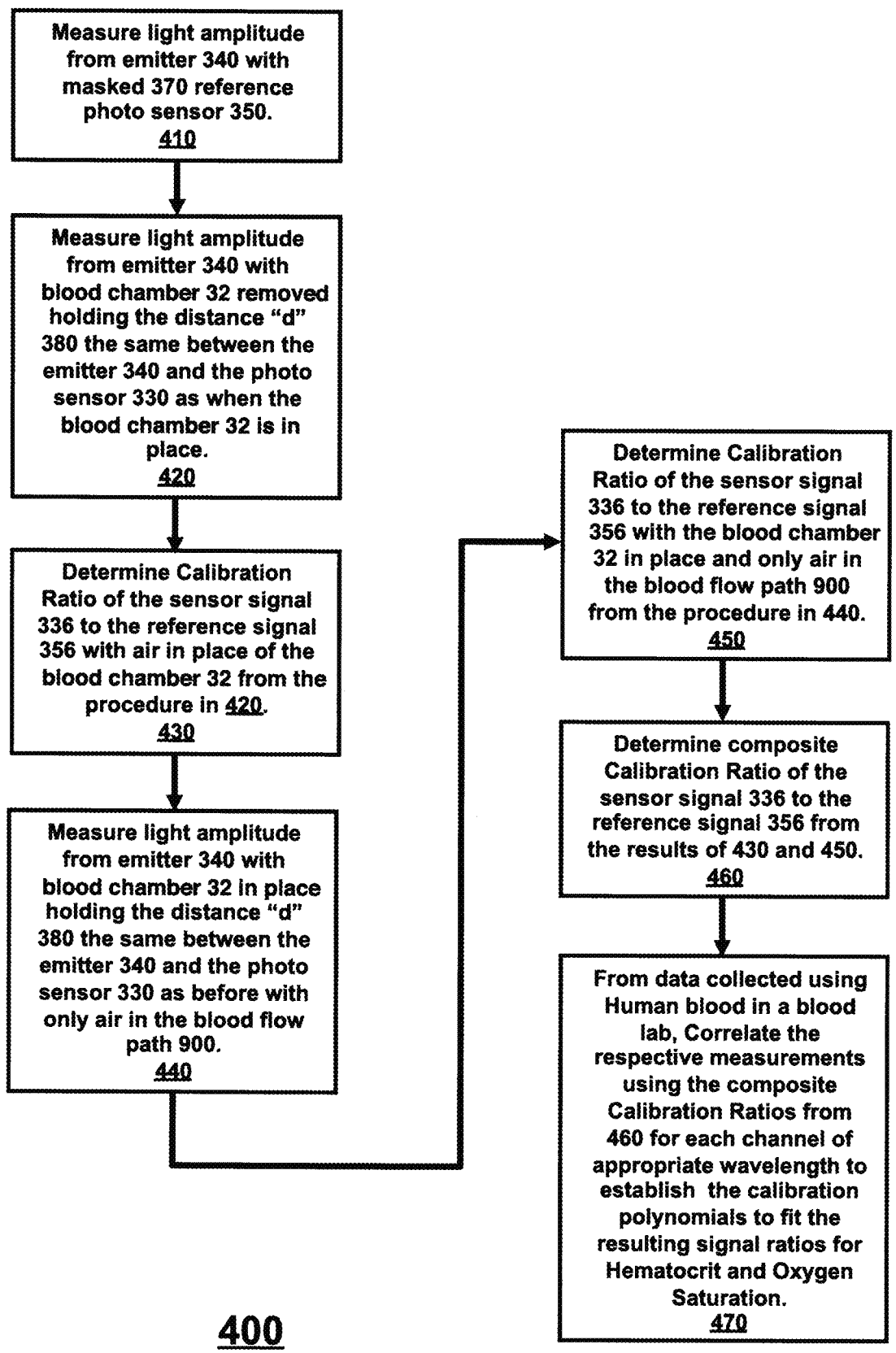
FIG. 4 is a flowchart referring to the schematic of FIG. 3 and describing the calibration of the blood monitoring system.

The schematic illustration of an embodiment of the blood monitoring system 14 in FIG. 3 includes a memory 320 for storing calibration parameters and executable instruction (such as instructions programmed to perform the steps shown in FIG. 4) used by the controller 310. The calibration parameters and executable instructions compensate for the attenuation of the light between the LED emitter 340 and the photo sensor 330 across the fixed distance "d" when there is no blood flood in the path 900.

In the embodiment of FIG. 3, the memory 320 stores a log of the calibration parameters used by the controller 310. The log may be used for system diagnostic purposes. For example, the memory 320 may keep a running log of compensation parameter values needed to normalize the sensor signal 336. If the log evidences the compensation required to normalize the sensor signal 336 is gradually increasing while the reference signal 356 from the reference photo sensor 350 is gradually decreasing over time, then the logged data suggests the LED emitter 340 is failing or burning out and needs to be replaced. In the illustrated embodiment of FIG. 3, the controller 310 is programmed to detect diagnostic events based upon the log of the calibration parameters used by the controller 310, and to alert operators.

In the embodiment of FIG. 3, the controller 310 performs a calibration to generate a new set of calibration parameters for each new blood channel used.

The controller 310 may include various components, such as a processor, non-transitory computer readable medium for storing computer code/programs to perform measurement method and/or calibration methods provided throughout in this disclosure, as well as user interface devices, such as keyboard, mouse, touchpad, displays, speakers and the like. For example, in the embodiment illustrated in FIG. 3, program memory 320 is a non-transitory computer readable medium. Serial interface 311 in FIG. 3 is an example of a communications interface for the controller 310. It passes the blood data developed by the monitoring system to the outside world for display and further analysis. Such as data port can be any of a variety of known formats and interfaces, including RS-232, Universal Serial Bus (UBS) and the like.

In the embodiment illustrated in FIG. 1, the blood data is delivered to the display 36 via cable 37, where the data is used to generate a graphical display of information useful to the clinician such as hematocrit values as suggested in FIG. 2. An example of a suitable display is, for example, the display of the Crit-Line Monitor III by Fresenius Medical Care, North America, Waltham, Mass.

As an alternative or in addition to the cable 37 in FIG. 1 for communicating data, the controller 310 may be coupled to a communication module that enables the transmitting and/or receiving of data and/or other information that may be controlled or used by the controller 310 and/or stored on the memory 320. In an embodiment, the communication module 318 includes a wireless transceiver that wirelessly transmits or receives the data or other information. In an example, the wireless transceiver enables wireless communication between the blood monitoring system 14 and the dialysis treatment system 12, or component thereof, performing the dialysis treatment and/or other peripheral devices that record or otherwise use data or other information concerning the dialysis treatment.

In an embodiment, the communication module 318 includes components for short-range wireless communications between the blood monitoring system 14 and the dialysis treatment system 12 via known short-range wireless technology protocol such as, for example, a Bluetooth protocol or an RFID protocol—e.g., a near field communication (NFC) protocol. In other embodiments, wireless communication to and from the blood monitoring system 12 may be facilitated using other wireless technologies, such as via WiFi and/or via an implementation utilizing telecommunication networks.

In connection with the transmission, either via cable 37 or via wireless transmission, the data may be secured and/or encrypted via the controller 310 using appropriate security and encryption protocols according to applicable laws and regulations governing transmission of sensitive data and/or protected medical information.

The blood monitoring system 14 eliminates the need for temperature-based measurements to calibrate or normalize the sensor signal 336. By directly measuring a portion of light emitted by the LED emitter 340 for use in compensating for changes in the light caused by effects such as temperature changes, the system does not need to wait long for the LED emitter 340 temperatures to stabilize before performing measurements.

Additionally, normalizing the sensor signal 336 using direct measurement of the emitted light keeps the controller 310 in proper calibration for a much longer time, making the life cycle of the system 14 longer. This approach also allows the use of lower cost LEDs (e.g., LEDs having higher variations in light intensity than would otherwise be possible) for LED emitter 340, allowing for reduced development time of many additional possible wavelengths for measuring additional blood characteristics.

The LED emitter 340 may be an array of diodes such that the emitted light comprises a plurality of wavelengths that enters the blood chamber 32 from a first side, passes through the blood flow channel 900 and exits the blood chamber from a second side. The sensor 330 on the second side of the blood chamber 32 receives the light from the LED emitter 340 after the amplitude of its plurality of wavelength has been affected by passing through the blood flow channel 900. The reference photo sensor 350 directly measures the light from the array comprising the LED emitter 340. The mask 370 ensures that only light from the LED emitter 340 arrives at the reference photo sensor 350. The controller 310 controls the measurement hardware and compensates measurements from the sensor 330 based upon measurements from the reference photo sensor 350, for example by measuring a ratio between readings from the reference photo sensor 350 and the sensor 330 prior to blood entering the blood chamber 32, and applying the ratio to readings from sensor 330 during dialysis while blood is in the channel 900.

Notably, the intensity of emitted light is inversely proportional to the square of the distance it travels. Thus, the distance "d" 380 between the LED emitter 340 and the sensor 330 must remain constant so that any change in intensity of sensed light during the calibration process and during actual usage is dependent entirely on the medium between the sensor 330 and LED emitter 340 and not characteristics of light propagation. The distance "d" is selected to be the distance separating the LED emitter 340 and the sensor 330 when the blood chamber 32 is inserted into the jaw of the clip assembly 34, which include opposing arms housing the LED emitter 340 and the sensor 330. The arms of the clip assembly 34 flex so that they can function as a jaw or clamp fitted over the blood chamber 32 at an area of the blood chamber that serves as a window into the blood flow channel 900. Because the arms flex, the distance between the LED emitter 340 and the sensor 330 is variable unless it is fixed such as, for example, by positioning the blood chamber 32 in the jaw formed by the arms of the clip assembly 34.

Referring now to calibrating the monitoring system 14, FIG. 4 illustrates an embodiment of a calibration method 400. The method 400 begins at block 410 by obtaining amplitude measurements at the reference photo sensor 350 of the light from the LED emitter 340 and sending the resulting reference signal 356 (FIG. 3) to the controller 310. At block 420 of FIG. 4, the sensor 330 obtains measurements of light from the LED emitter 340 with the blood chamber 32 removed while holding the distance "d" 380 between the sensor and the LED emitter. The sensor 330 provides a sensor signal 336.

At block 430, the controller 310 determines a calibration ratio between each processed signal derived from reference signal 356 and the sensor signal 336 while nothing is between the sensor 330 and the LED emitter 340 held at the distance "d" 380.

At block 440, the photo sensor 330 obtains a light measurement from LED emitter 340, with the blood chamber 32 in the measurement path but with the blood flow channel 900 being empty (only air present).

At block 450, a controller 310 determines a calibration constant between each received and processed reference signal 356 and each sensor signal 336 with the blood chamber 32 in the light path but with nothing in the blood flow path 900 except air.

At block 460, the controller 310 determines a composite ratiometric Calibration Coefficient for each wavelength from the measurements at blocks 430 and 450. These composite Calibration Coefficients are used to normalize the measurements of light across the blood flow 900 in the blood chamber 32 by illuminating the blood with LED emitters 340 and receiving the modified amplitude of the light at the photo sensor 330 through the absorption and scattering of the blood. At the same time, variations in the amplitudes of the LED emitters 340 themselves are measured by the reference photo sensors 350 to complete the normalization.

The modeling of calibration and compensation functions for each wavelength is illustrated as follows:

Light measured by the reference photo sensor 350 may be a function according to Beer's Law:

$$i_r = I_O e^{-\alpha_{E_r} d_{E_r}} \tag{1}$$

where, $i_r$ is measurement of light intensity at the reference photo sensor 350, $I_O$ is the actual intensity of light radiated by the LED emitter 340, $\alpha_{E_r}$ is light loss coefficient from the LED emitter 340 to the reference photo sensor due to the material of the dome 360, and $d_{E_r}$ is the distance light travels from LED emitter 340 to the reference photo sensor 350 in dome 360.

$$e^{-\alpha_{E_r} d_{E_r}}$$

may be considered a constant $K_r$.

Which simplifies to:

$$i_r = I_O K_r \tag{2}$$

Beer's Law equation may be similarly applied for light measured by the photo sensor 330 with more loss components:

$$i_m = I_O e^{-\alpha_{E_m} d_{E_m}} e^{-\alpha_{m_1} d_{m_1}} e^{-\alpha_{m_2} d_{m_2}} e^{-\alpha_{p_1} d_{p_1}} e^{-\alpha_b d_b} e^{-\alpha_{p_2} d_{p_2}} \quad (3)$$

where, $i_m$ is measurement of light intensity at the photo sensor 330, $\alpha_{E_m}$ is light loss coefficient from the LED emitter 340 to the epoxy-air boundary of the dome 360 along a ray toward sensor 330 within the dome due to the material of the dome 360 (in the example, the same as $\alpha_{E_r}$), $d_{E_m}$ is the ray distance light travels from LED emitter 340 to exit the transparent dome 360, $\alpha_{m_1}$ is the light loss coefficient from the exit (surface) of the dome 360 to the side wall of the blood chamber 32 on the first (illumination) side due to the medium material light properties through which the light travels, $d_{m_1}$ is the distance light travels from the surface of the dome 360 to the blood chamber 32 on the first (illumination) side, $\alpha_{m_1}$ is light loss coefficient from the second (receiving) side wall of blood chamber 32 toward the photo sensor 330 due to the medium material light properties through which the light travels, $d_{m_2}$ is the distance light travels from second side (receiving) wall of the blood chamber 32 to the photo sensor 330, $\alpha_{p_1}$ is light loss coefficient of first side (illumination) thickness of the blood chamber 32 outside wall to the blood flow channel 900 based on the light propagation properties of the blood chamber 32 material, $d_{p_1}$ is the distance light travels in the first side (illumination) from the outside side wall of the blood chamber 32 to the blood flow channel 900, $\alpha_b$ is light loss coefficient of the blood in the blood flow channel 900, $d_b$ is the distance light travels through the blood in the blood flow channel 900 (which is the inside channel thickness of the blood flow channel 900), $\alpha_{p_2}$ is light loss coefficient of second side (receiving) thickness of the blood chamber 32 from the blood flow channel 900 to the outside wall based on the light propagation properties of the blood chamber 32 material, and $d_{p_2}$ is the distance light travels in the second side (receiving) from the blood flow channel 900 to the outside side wall of the blood chamber 32.

Equation (3) can be simplified to:

$$i_m = I_O K_m e^{-\alpha_{p_1} d_{p_1}} e^{-\alpha_b d_b} e^{-\alpha_{p_2} d_{p_2}} \quad (4)$$

Combining equations (2) and (4):

$$\frac{i_m}{i_r} = \frac{I_O K_m e^{-\alpha_{p_1} d_{p_1}} e^{-\alpha_b d_b} e^{-\alpha_{p_2} d_{p_2}}}{I_O K_r} \quad (5)$$

Canceling $I_O$ from equation (5) yields:

$$\frac{i_m}{i_r} = \frac{K_m e^{-\alpha_{p_1} d_{p_1}} e^{-\alpha_b d_b} e^{-\alpha_{p_2} d_{p_2}}}{K_r} \quad (6)$$

Without the presence of blood and the blood chamber in the flow channel 900, the ratio becomes:

$$\frac{i_m}{i_r} = \frac{K_m}{K_r} \quad (7)$$

During calibration, the Composite Calibration light propagation constant for each wavelength $S_c$ for $K_m/K_r$ may be derived by taking calibration measurements of the reference photo sensor 350 and the sensor 330 (obtaining $i_m/i_r$), without the presence of blood and the blood chamber in the flow channel and holding constant the distance "d" (380) between the LED 340 and the photo sensor 330.

Plugging in $S_c = K_m/K_r$ into equation (6), the function for photo sensor 330 measurements becomes:

$$i_m = (S_c i_r) e^{-\alpha_{p_1} d_{p_1}} e^{-\alpha_b d_b} e^{-\alpha_{p_2} d_{p_2}} \quad (8)$$

where $$e^{-\alpha_{p_1} d_{p_1}} e^{-\alpha_{p_2} d_{p_2}}$$

is also constant.

Assigning constant $$K_p = e^{-\alpha_{p_1} d_{p_1}} e^{-\alpha_{p_2} d_{p_2}},$$

$K_p$ may be derived by taking calibration measurements of the reference photo sensor 350 and the photo sensor 330, with the blood flow channel 900 of the blood chamber 32 being empty and present in the optical path between LED emitter 340 and sensor 330.

During calibration, $K_p$ can be derived for each new blood chamber 32 with the blood flow channel 900 being empty. Assuming tight controls are possible in the molding of the blood chamber 32, $K_p$ can be assumed to be constant across different blood chambers unless there is a change in the molding properties of the blood chamber. This is another feature of this embodiment in that changes in the blood chamber 32 can be made and the blood monitoring systems 14 in the field can compensate for any change in calibration rather than having to return the systems to the factory for completing calibration adjustments.

Thus, equation (8) can be simplified to:

$$i_m = (S_c i_r) K_p e^{-\alpha_b d_b} \quad (9)$$

and $$K_p = \frac{i_m}{(S_c i_r)} \quad (10)$$

when $\alpha_b$ equals zero (no blood equals blood chamber empty) and $d_b$ is the normal light path length through an empty blood chamber which is in the sensor.

Additionally, $e^{-\alpha_b d_b}$ is a function dependent upon blood characteristics, and may be profiled independently ahead of time and stored in controller 310 for use, for example, by using a standard set of blood samples for calibration in labs, and pre-programming the profile function of $e^{-\alpha_b d_b}$ into controller 310, as algorithms or a set of lookup tables. A set of these calibrations is unique and required for each active wavelength.

As $d_b$ is also assumed to be constant and could be measured and/or inputted into controller 310, the controller 310 can solve for $\alpha_b$:

$$\alpha_b = \frac{-\ln\frac{i_m}{(S_c i_r) K_p}}{d_b} \quad (11)$$

Equation (11) can be used to derive $\alpha_b$ for blood of various blood characteristics at various concentrations and different light wavelengths. For example, polynomial fitting may be used to derive HCT value, using the following:

$$HCT = A\left(\frac{\alpha_{800}}{\alpha_{1300}}\right)^2 + B\left(\frac{\alpha_{800}}{\alpha_{1300}}\right) + C \quad (12)$$

where, $\alpha_{800}$ is $\alpha_b$ derived from measurements taken at a wavelength of 800 nm emitted from LED emitter 340, $\alpha_{1300}$ is $\alpha_b$ derived from measurements taken at a wavelength of 1300 nm emitted from LED emitter 340.

Standard samples of known HCT levels are measured in Human blood and are used to derive the HCT calibration polynomial coefficients A, B, and C through regression techniques, These coefficients A, B, and C are then programmed into the controller 310 algorithm for ongoing HCT calculations.

During operation, the controller 310 may take measurements to derive $\alpha_{800}$ and $\alpha_{1300}$ for a specific blood sample of a specific patient, and solve for the HCT results.

Thus, according to the embodiments above, the differential measurement system based upon direct LED emitter 340 light monitoring and the resulting normalization of photo sensor 330 readings can provide accurate blood characteristic measurements with simple calibration.

The identical system can be used with the ratio of similarly derived light loss coefficients for an approximately 660 nm wavelength and an approximately 800 nm wavelength to create the model and algorithms for measurement of oxygen saturation of the blood.

Figure 5:
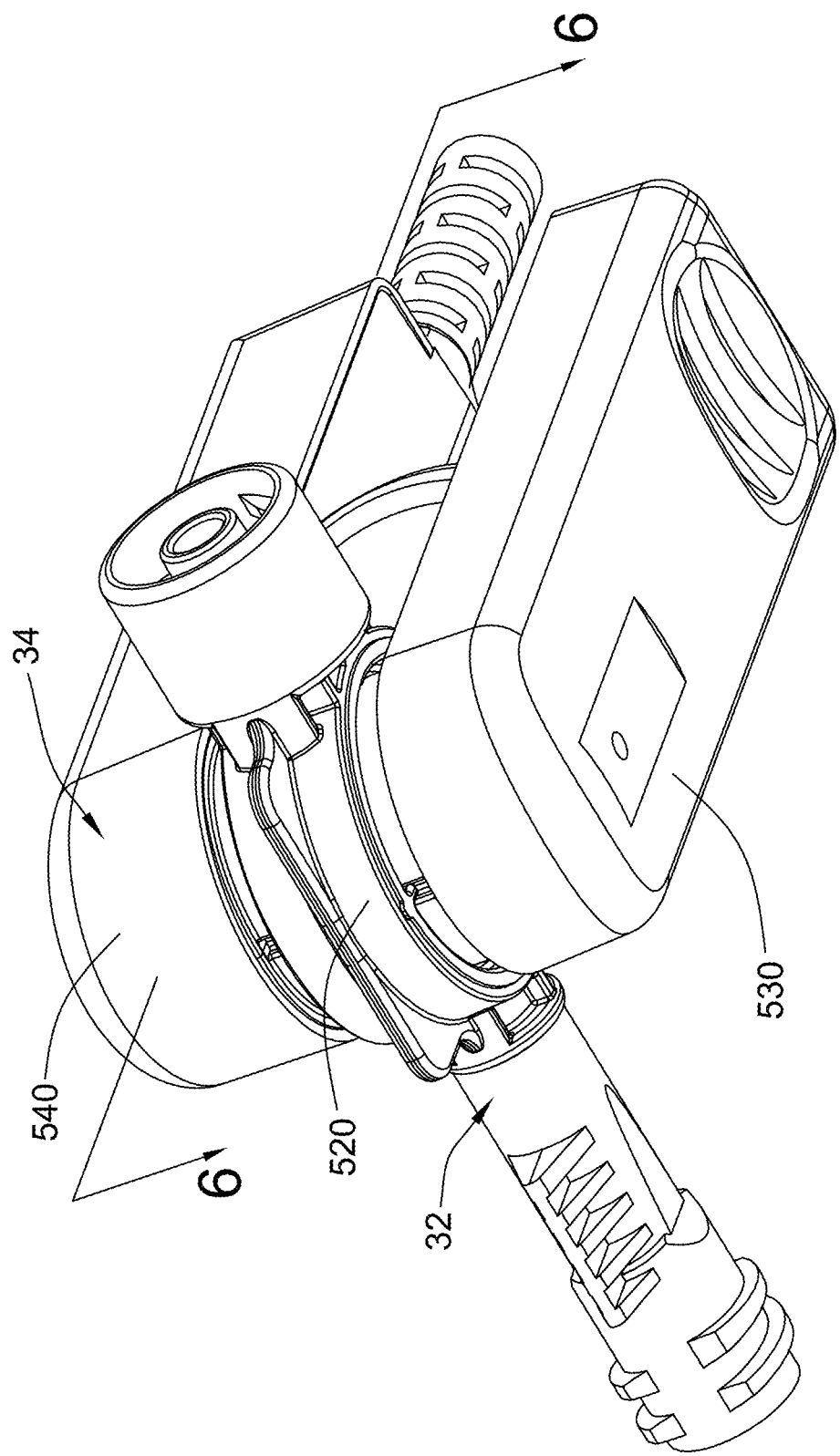
FIG. 5 is an isometric illustration of a clip assembly mated to a blood chamber according to the blood monitoring system in FIG. 1.

Turning to FIG. 5, an enlarged and isolated view is shown of the clip assembly 34 mated to the blood chamber 32 as shown more generally in FIG. 1. The clip assembly 34 may incorporate components of the blood monitoring system 14 as discussed hereinafter. In accordance with one or more embodiments, the LED emitter 340 (e.g., an array of LEDs) is located on a circuit board within one side 530 of the clip assembly 34, while the photo sensor 330 is located on a circuit board within the opposing side 540 of the assembly. The reference photo sensor 350 is co-located with the LED emitter 340 on side 530. When the clip assembly 34 is attached to the blood chamber 32, light emitted from the first side 530 by the LED emitter 340 passes through the blood flow path 900 of the blood chamber 32 and is detected by the photo sensor 330 on the opposing side 540 of the clip assembly. Various physical properties of blood flowing through the chamber 520 in the blood flow path affect the intensity of the light received at the photo sensor 330 on the second side 540.

Figure 6:
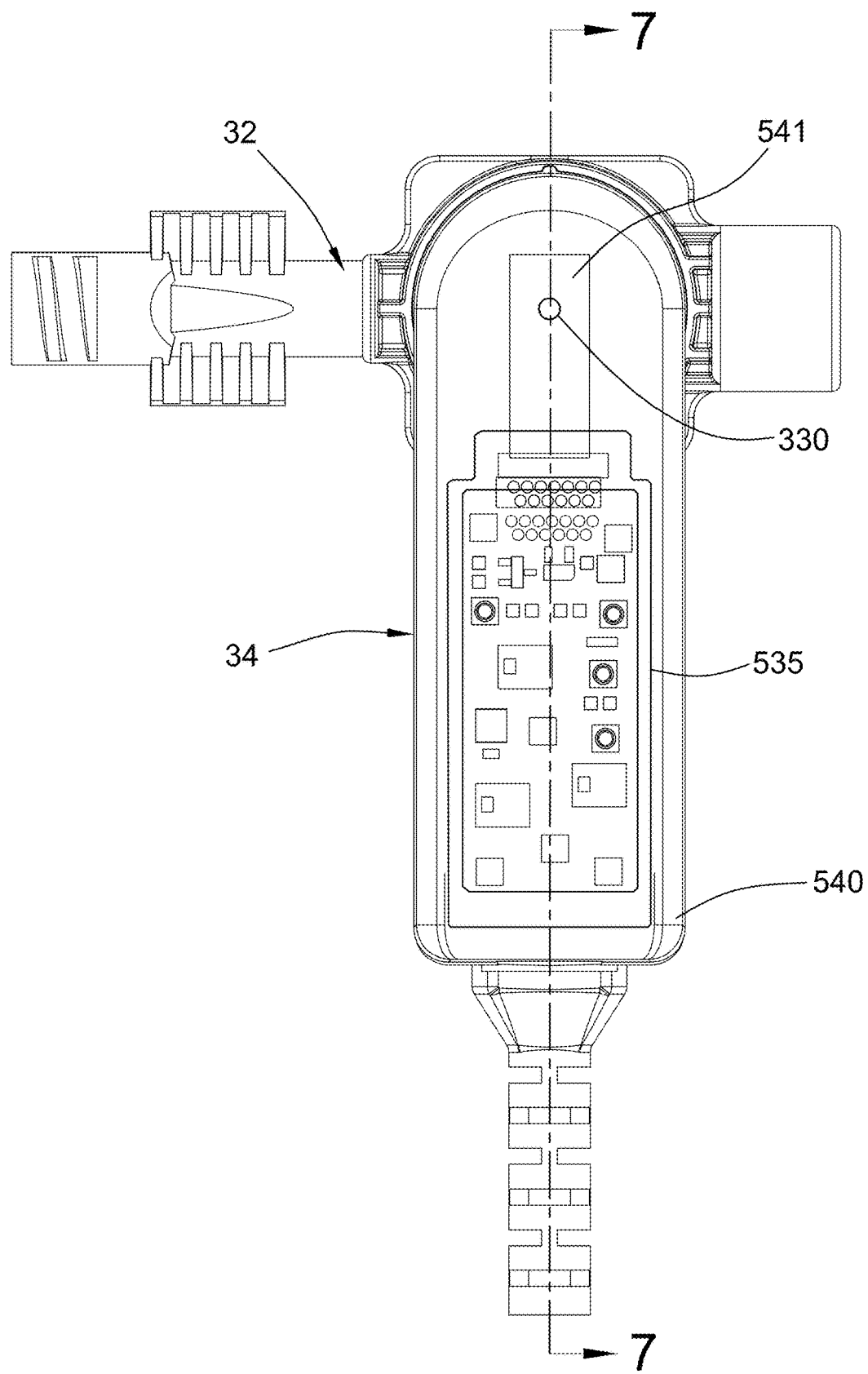
FIG. 6 is a plan view of the clip assembly and mating blood chamber taken along the line 6-6 in FIG. 5, generally illustrating in gray scale a circuit board housed by the clip assembly and including the hardware schematically illustrated in FIG. 3.

FIG. 6 illustrates the clip assembly 34 and mating blood chamber 32 in FIG. 5, showing the interior of the side 540 of the clip in accordance with an embodiment. The circuit boards 535 and 541 are housed in side 540 of the assembly 34. Circuit board 541 supports the photo sensor 330 and circuit board 535 supports substantially all of the circuitry illustrated in FIG. 3.

Figure 7:
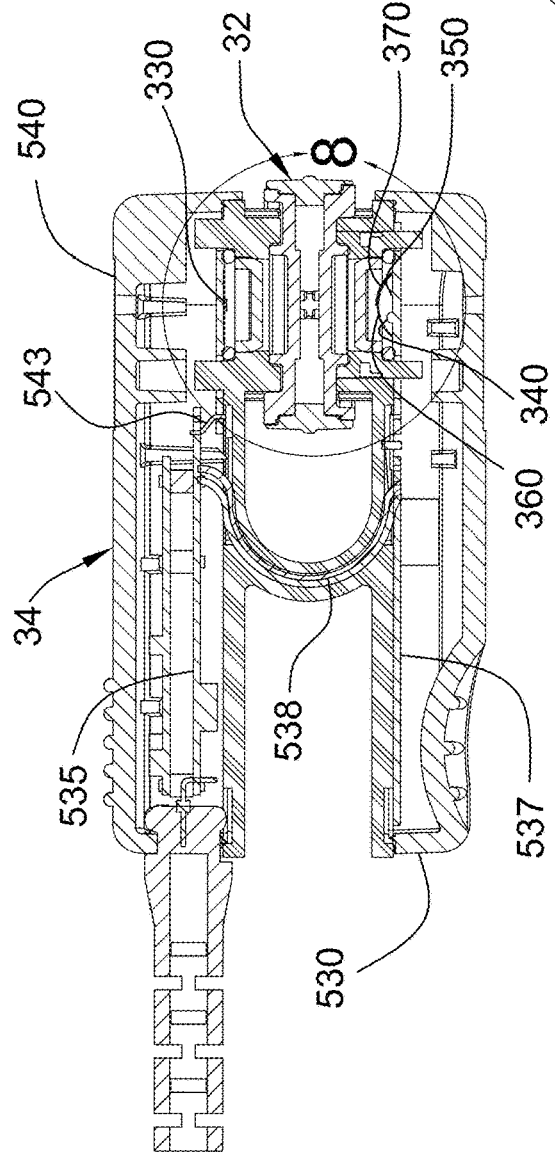
FIG. 7 is a sectional view of the clip assembly and mating blood chamber taken along the line 7-7 of FIG. 6, showing details of the area where the clip assembly and blood chamber mate.

A circuit board 537 is housed in side 530 of the clip assembly 34 as best illustrated in the cross sectional view of FIG. 7. The circuit boards 536 and 537 support the light transmitter portion of the monitoring system illustrated in FIG. 3. In particular, the circuit board 536 supports the light emitters 340 (e.g., LEDs) and the reference sensor 350 in an area within the side 530 of the clip assembly 34 that positions the emitters and the photo sensor 330 on opposite sides of the blood chamber 32 as schematically illustrated in FIG. 3. A ribbon cable 538 connects the circuit board 537 to the circuitry supported on the circuit board 535 housed in side 540.

The cross section of the mated clip assembly 34 and blood chamber 32 illustrated in FIG. 7 provides additional information about the spatial relationships among the light emitters 340, the photo sensor 330 of the clip assembly 34 and the blood flow path 900 of the blood chamber 32. One side 530 of the clip assembly 34 mates to one side of the blood chamber 32, while the second side 540 of the clip assembly mates to the other side of the blood chamber. The first side 530 of the clip assembly 34 includes the circuit boards 537 and 536 with mounted light emitters 340 (e.g., LEDs), while the second side 540 contains the photo sensor 330 for detecting light passing through the blood flow path 900 of the blood chamber 32.

Figure 8:
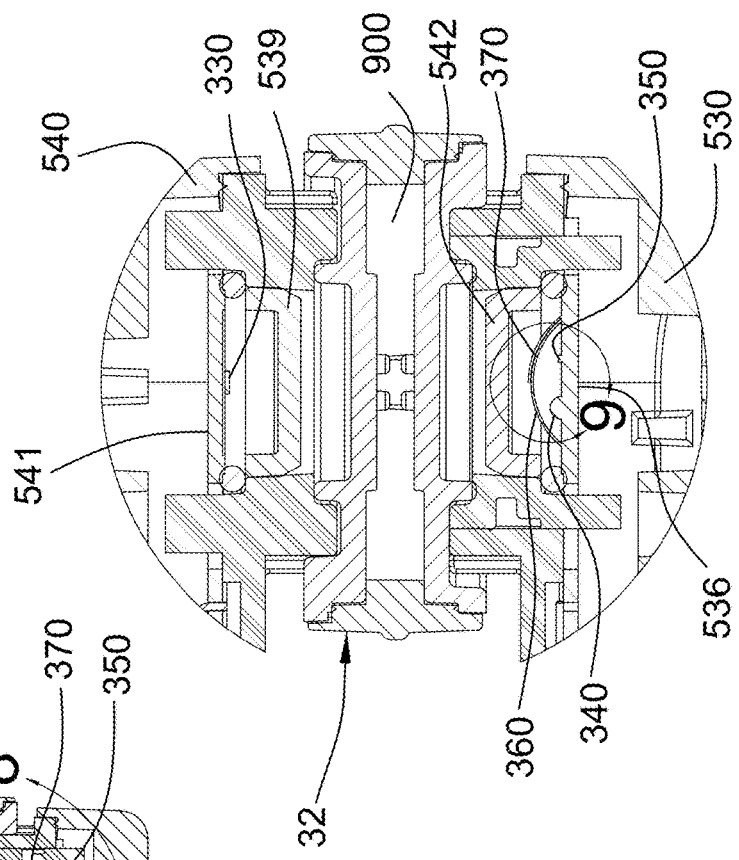
FIG. 8 is an isolated and enlarged view of the Detail A in the sectional view of the clip assembly and mating blood chamber as illustrated in FIG. 7, showing a sensor for directly measuring light from a LED in the clip assembly.

FIG. 8 is an enlarged view of the area in FIG. 7 that includes the interface between the sides 530 and 540 of the clip assembly 34 and the blood chamber 32. Each of the sides is an arm of the clip assembly 34. On the first side 530 (or arm 530) of the clip assembly 34, the circuit board 536 supports both the LED emitters 340 and the reference photo sensor 350 under a light diffusing window 542. Similarly, a light diffusing window 539 in the side 540 allows light from the emitters 340 that passes through the blood chamber 34 to be received by the photo sensor 330 mounted on a circuit board 541 within the side 540. A ribbon cable 543 best seen in FIG. 7 connects the circuit board 541 to the board 535. Further detail of the clip assembly 34 and the blood chamber 32 can be found at U.S. Pat. No. 8,743,354, which is herein incorporated by reference in its entirety and for everything it teaches. Specifically, the embodiment of the clip assembly 34 and the blood chamber 32 illustrated herein is shown in further detail in FIGS. 25A through 29E of the '354 patent.

The partially transparent epoxy dome 360 covers the emitter 340 and reference sensor 350. A portion of dome 360 is used as the mask 370, which shields the reference sensor 350 from any externally reflected light or other light other than direct light from the LED emitter 340. The reference photo sensor 350 may be each be a Silicon or an Indium Gallium Arsenide photodiode, or each an array of Silicon or Indium Gallium Arsenide photodiodes, such as those manufactured by Hamamatsu Photonics K.K., Hamamatsu City, Japan.

Light passes from the LED emitter 340 through the unmasked portion of the dome 360 to the blood chamber 32 and the blood flow path 900 inside the chamber to the photo sensor 330 located on the second side (receiving side or arm 540) of the clip assembly 34. Blood in path 900 and its parameters absorb and scatter the light, thereby modifying the amplitudes of light at different wavelengths arriving at the photo sensor 330.

Figure 9:
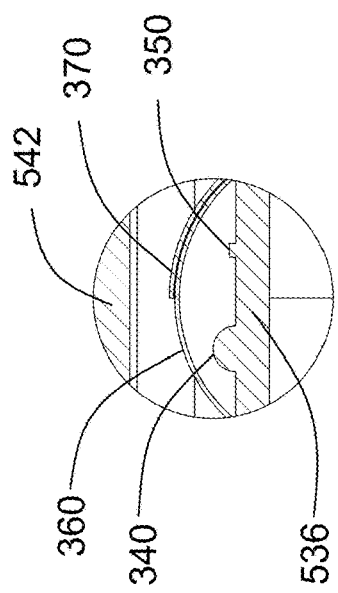
FIG. 9 is an isolated and further detail of the detail shown in FIG. 8 of the clip assembly and mating blood chamber, showing the structure the LED mounted to a circuit board housed in the clip assembly and adjacent the sensor for directly measuring light from the LED.
Figure 11:
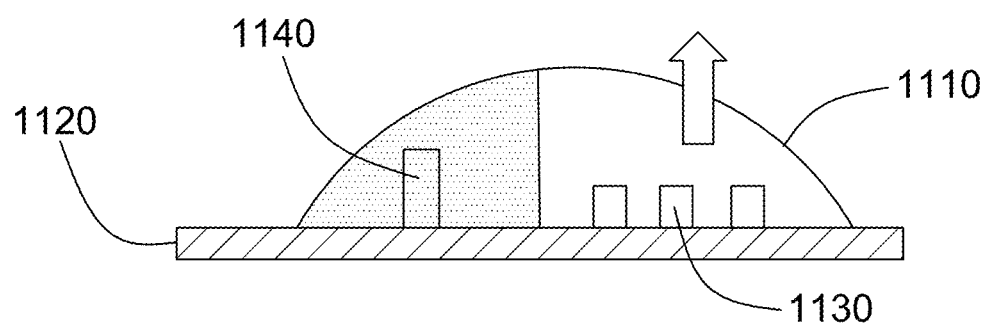
FIG. 11 illustrates another alternative embodiment for directly sensing the light from the light sources in the clip assembly.
Figure 12:
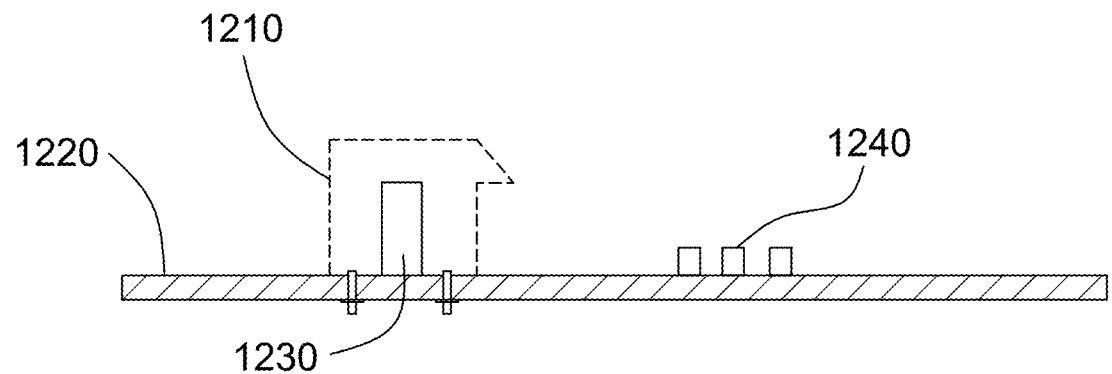
FIG. 12 illustrates still another alternative embodiment for directly sensing the light from the light sources in the clip assembly.

In still further detail, an enlarged and isolated view of the dome 360 is shown in FIG. 9. The epoxy dome 360 is placed on the circuit board 536, covering the light emitter 340 and the reference photo sensor 350. The portion of the dome 360 over the reference photo sensor 350 is coated with an opaque surface 370 so that any reflected light from outside dome 360 that otherwise might reach the reference photo sensor 350 is blocked. In this embodiment, the reference photo sensor 350 is placed on the circuit board 536 in a conventional manner such that its direction of primary detection is approximately perpendicular to the light emitter 340. However, sufficient light from the light emitter 340 reaches the reference photo sensor 350 to effectively detect light from the emitter when the detector is protected from ambient or external reflected light by the mask 370. Alternatively, and as illustrated in FIGS. 11 and 12 discussed hereinafter, a reference photo sensor (1140 and 1230, respectively) can be mounted to the circuit board 536 to face the light emitter 340, which then increases the sensitivity and noise immunity of the sensor. However, the edge mounting of the sensor is typically a more expensive mounting technique.

Additional embodiments are described with reference to FIGS. 10-13.

Figure 10A:
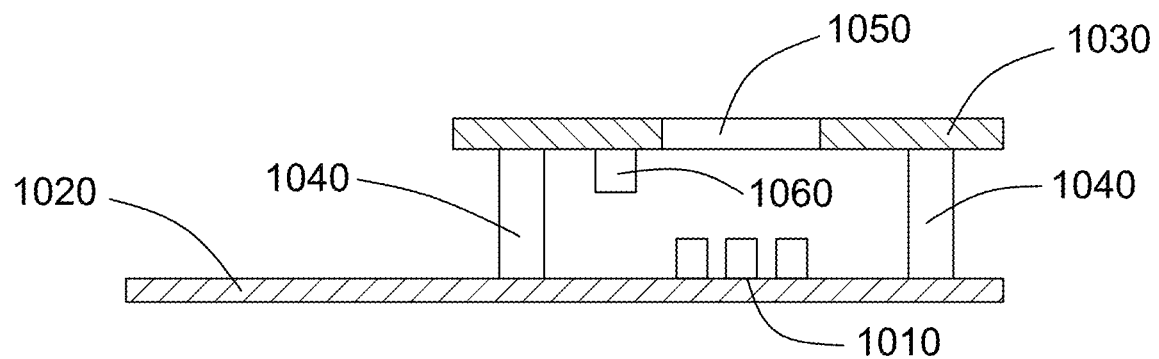
FIGS. 10*a* and 10*b* illustrate an alternative embodiment of the clip assembly with respect to that illustrated in FIGS. 7-9 for directly sensing light from the light source in the clip assembly.
Figure 10B:
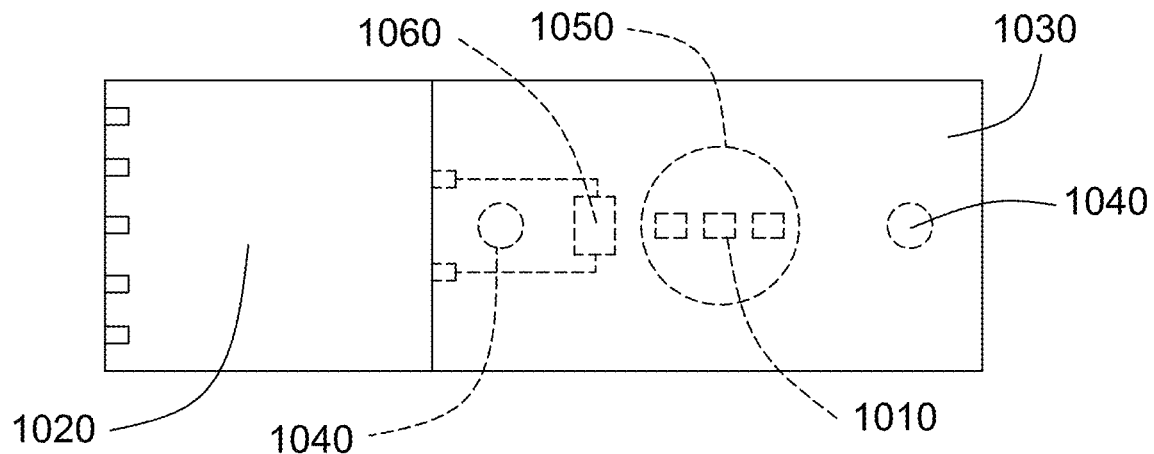

Referring to FIGS. 10a and 10b, an array of LEDs 1010 are mounted to a circuit board 1020, which is located approximately where the circuit board 536 is located in FIGS. 6-9. The LEDs 1010 need not be of any particular brightness or quality standard. In this embodiment, a shield 1030 is spaced at a fixed distance from the circuit board 1020 through the use of spacers 1040. The shield 1030 is made of material such that it blocks all reflected light from the LEDs 1010, which light passes through an opening 1050 in the shield that allows the light to pass to the blood chamber. A reference photo sensor 1060 is mounted on the underside of the shield 1030. Not shown in FIG. 10 is the blood chamber 32 or the photo sensor 330 in the arm of the clip assembly 34 opposite the arm housing the LEDs 1010. The calibration and measurement work in a similar manner as described above in reference to the embodiment of FIGS. 6-9, using the difference in light intensity between the reference photo sensor 1060 and the photo sensor 330 to determine levels of hematocrit, oxygen saturation, and/or other blood constituents.

In another alternative embodiment, not shown, the reference photo sensor is placed directly next to the LEDs on the circuit board, or sufficiently close to the LEDs that the intensity of the direct light from the LEDs themselves is much greater than any optical noise from reflections and/or ambient light. Using such an embodiment increases the sensitivity of the reference photo sensor and may reduce or render insignificant the optical noise such that the mask is unnecessary.

The embodiment in FIG. 11 uses an epoxy dome 1110 like the embodiment of FIGS. 6-9. The dome 1110 is placed on the circuit board 1120, which is positioned in the clip assembly 34 similarly to the position of the circuit board 536 in FIGS. 6-9. The dome 1110 covers the array of LEDs 1130 and a reference photo sensor 1140. The reference photo sensor 1140 is preferably a photo diode placed on its edge, so that the sensor more directly faces the light emitted by the LEDs 1130 then it would otherwise if mounted flat on the circuit board 1120. The portion of the dome 1110 over the reference photo sensor 1140 is coated with an opaque material, so that any external reflected light that otherwise might reach the reference photo sensor 1140 (both visible and infrared) is blocked. Not shown in FIG. 11, the blood chamber 32 runs parallel to the circuit board 1120, such that light (upwardly pointing arrow) from the LEDs 1130 passes through the non-opaque portion of the dome 1110, through the blood chamber, and is detected by the photo sensor (not shown) in the opposing arm of the clip assembly 34.

In accordance with another embodiment, a solid enclosure 1210 in FIG. 12 is mounted on a circuit board 1220 positioned in the arm 530 of the clip assembly 34 similarly to the position of the circuit board 535 in FIGS. 6-9. Like the embodiment illustrated in FIG. 11, the reference photo sensor 1230 is placed on its edge on the circuit board 1220. The solid enclosure 1210 surrounds the reference photo sensor 1230 on all sides, with the exception of an opening facing the array of LEDs 1240. In this embodiment, the solid enclosure 1210 may be made of metal, or other material that is impervious to all light. Not shown in FIG. 12, the blood chamber 34 is oriented to be parallel to the circuit board 1220, such that light from the LEDs 1240 passes through the blood chamber for measurement by the photo sensor on an opposing side.

Although the embodiments of FIGS. 11 and 12 are illustrated as including masks or shrouds intended to optically isolate the reference photo sensors, the increased sensitivity achieved by edge mounting the sensors to the circuit boards may increase the signal to noise immunity of the sensor such that the masks or shrouds are not required.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A measurement system for measuring blood characteristics, the system comprising:
   an emitter disposed on a first side of a blood chamber, wherein the emitter is configured to emit light through blood in the blood chamber;
   a sensor disposed on a second side of the blood chamber, wherein the sensor is configured to detect light from the emitter that has passed through blood in the blood chamber;
   a reference sensor disposed on the first side of the blood chamber, wherein the reference sensor is configured to detect light directly from the emitter, and wherein the reference sensor is positioned proximate to and in line of sight of the emitter so as to increase noise immunity of the measurement system; and
   a controller configured to normalize measurements from the sensor using measurements from the reference sensor, so as to compensate for emitter variability, wherein normalization of the measurements from the sensor using the measurements from the reference sensor is based on a composite ratiometric calibration coefficient for a wavelength of light corresponding to the emitter, wherein the composite ratiometric calibration coefficient is based on: (1) a calibration ratio between reference and sensor signals obtained while a blood chamber is not disposed between the emitter and the sensor; and (2) a calibration ratio between reference and sensor signals obtained while a blood chamber without blood is disposed between the emitter and the sensor.

2. The measurement system according to claim 1, wherein the reference sensor being positioned proximate to and in line of sight of the emitter so as to increase the noise immunity of the measurement system comprises the reference sensor being edge mounted on a same circuit board as the emitter.

3. The measurement system according to claim 1, wherein the reference sensor being positioned proximate to and in line of sight of the emitter so as to increase the noise immunity of the measurement system comprises the reference sensor being positioned directly next to the emitter on a same circuit board as the emitter.

4. The measurement system according to claim 1, further comprising:
   a mask for optically isolating the reference sensor from light other than light directly sourcing from the emitter, wherein the position of the reference sensor relative to the emitter increases the noise immunity of the measurement system independently of the mask.

5. The measurement system according to claim 1, wherein the controller is configured to generate a new set of calibration parameters when the blood chamber is replaced with another blood chamber.

6. The measurement system according to claim 1, further comprising:
   a memory configured to store a log of calibration parameters relating to the emitter;
   wherein the controller is configured to analyze the log of calibration parameters to detect a problem with the emitter.

7. The measurement system according to claim 1, wherein the controller is configured to use the normalized measurements to determine a hematocrit and/or an oxygen saturation of blood in the blood chamber.

8. The measurement system according to claim 1, wherein the measurement system is connected to or part of a dialysis system.

9. A measurement system for measuring blood characteristics, the system comprising:
   a plurality of emitters disposed on a first side of a blood chamber, wherein the plurality of emitters are configured to emit light corresponding to different wavelengths through blood in the blood chamber;
   a plurality of sensors disposed on a second side of the blood chamber, wherein the plurality of sensors are configured to detect light from the plurality of emitters that has passed through blood in the blood chamber;
   at least one reference sensor disposed on the first side of the blood chamber, wherein the at least one reference sensor is configured to detect light directly from the plurality of emitters, and wherein the at least one reference sensor is positioned proximate to and in line of sight of the plurality of emitters so as to increase noise immunity of the measurement system; and
   a controller configured to normalize measurements from the plurality of sensors using measurements from the at least one reference sensor, so as to compensate for emitter variability, wherein normalization of the measurements from the plurality of sensors using the measurements from the at least one reference sensor is based on a plurality of composite ratiometric calibration coefficients, wherein each composite ratiometric calibration coefficient corresponds to a respective wavelength of light, and wherein each composite ratiometric calibration coefficient is based on: (1) a respective calibration ratio between reference and sensor signals obtained while a blood chamber is not disposed between a respective emitter and a respective sensor; and (2) a respective calibration ratio between reference and sensor signals obtained while a blood chamber without blood is disposed between the respective emitter and the respective sensor.

10. A measurement method for measuring blood characteristics, the method comprising:
    emitting, by an emitter of a measurement system, light through blood in a blood chamber, wherein the emitter is disposed on a first side of the blood chamber;
    detecting, by a sensor of the measurement system, light from the emitter that has passed through blood in the blood chamber, wherein the sensor is disposed on a second side of the blood chamber;
    detecting, by a reference sensor of the measurement system, light directly from the emitter, wherein the reference sensor is disposed on the first side of the blood chamber, and wherein the reference sensor is positioned proximate to and in line of sight of the emitter so as to increase noise immunity of the measurement system; and
    normalizing, by a controller of the measurement system, measurements from the sensor using measurements from the reference sensor, so as to compensate for emitter variability, wherein normalizing the measurements from the sensor using the measurements from the reference sensor is based on a composite ratiometric calibration coefficient for a wavelength of light corresponding to the emitter, wherein the composite ratiometric calibration coefficient is based on: (1) a calibration ratio between reference and sensor signals obtained while a blood chamber is not disposed between the emitter and the sensor; and (2) a calibration ratio between reference and sensor signals obtained while a blood chamber without blood is disposed between the emitter and the sensor.

11. The measurement method according to claim 10, wherein the reference sensor being positioned proximate to and in line of sight of the emitter so as to increase the noise immunity of the measurement system comprises the reference sensor being edge mounted on a same circuit board as the emitter.

12. The measurement method according to claim 10, wherein the reference sensor being positioned proximate to and in line of sight of the emitter so as to increase the noise immunity of the measurement system comprises the reference sensor being positioned directly next to the emitter on a same circuit board as the emitter.

13. The measurement method according to claim 10, wherein the position of the reference sensor relative to the emitter increases the noise immunity of the measurement system independently of use of a mask for optically isolating the reference sensor from light other than light directly sourcing from the emitter.

14. The measurement method according to claim 10, further comprising:
generating, by the controller, a first set of calibration parameters for the blood chamber; and
generating, by the controller, a second set of calibration parameters for another blood chamber.

15. The measurement method according to claim 10, further comprising:
storing, by a memory of the measurement system, a log of calibration parameters relating to the emitter; and
analyzing, by the controller, the log of calibration parameters to detect a problem with the emitter.

16. The measurement method according to claim 10, further comprising:
using, by the controller, the normalized measurements to determine a hematocrit and/or an oxygen saturation of blood in the blood chamber.

17. A non-transitory computer-readable medium having processor-executable instructions stored thereon for measuring blood characteristics, wherein the processor-executable instructions, when executed, facilitate:
emitting, by an emitter of a measurement system, light through blood in a blood chamber, wherein the emitter is disposed on a first side of the blood chamber;
detecting, by a sensor of the measurement system, light from the emitter that has passed through blood in the blood chamber, wherein the sensor is disposed on a second side of the blood chamber;
detecting, by a reference sensor of the measurement system, light directly from the emitter, wherein the reference sensor is disposed on the first side of the blood chamber, and wherein the reference sensor is positioned proximate to and in line of sight of the emitter so as to increase noise immunity of the measurement system; and
normalizing, by a controller of the measurement system, measurements from the sensor using measurements from the reference sensor, so as to compensate for emitter variability, wherein normalizing the measurements from the sensor using the measurements from the reference sensor is based on a composite ratiometric calibration coefficient for a wavelength of light corresponding to the emitter, wherein the composite ratiometric calibration coefficient is based on: (1) a calibration ratio between reference and sensor signals obtained while a blood chamber is not disposed between the emitter and the sensor; and (2) a calibration ratio between reference and sensor signals obtained while a blood chamber without blood is disposed between the emitter and the sensor.

18. The non-transitory computer-readable medium according to claim 17, wherein the reference sensor being positioned proximate to and in line of sight of the emitter so as to increase the noise immunity of the measurement system comprises the reference sensor being edge mounted on a same circuit board as the emitter.

19. The non-transitory computer-readable medium according to claim 17, wherein the reference sensor being positioned proximate to and in line of sight of the emitter so as to increase the noise immunity of the measurement system comprises the reference sensor being positioned directly next to the emitter on a same circuit board as the emitter.

20. The non-transitory computer-readable medium according to claim 17, wherein the position of the reference sensor relative to the emitter increases the noise immunity of the measurement system independently of a mask for optically isolating the reference sensor from light other than light directly sourcing from the emitter.

21. The non-transitory computer-readable medium according to claim 17, wherein the processor-executable instructions, when executed, further facilitate:
generating, by the controller, a first set of calibration parameters for the blood chamber; and
generating, by the controller, a second set of calibration parameters for another blood chamber.

22. The non-transitory computer-readable medium according to claim 17, wherein the processor-executable instructions, when executed, further facilitate:
storing, by a memory of the measurement system, a log of calibration parameters relating to the emitter; and
analyzing, by the controller, the log of calibration parameters to detect a problem with the emitter.

* * * * *